United States Patent

Speckbacher et al.

(10) Patent No.: US 7,544,215 B2
(45) Date of Patent: *Jun. 9, 2009

(54) NEUTRAL AND CATIONIC NAPHTHALENE AND COLORANTS FOR KERATIN FIBERS CONTAINING THESE COMPOUNDS

(75) Inventors: Markus Speckbacher, Mschaffenburg (DE); Hans-Juergen Braun, Ueberstorf (CH); Jessica Chassot, Chavannes-sous-Orsonnens (CH)

(73) Assignee: Wella AG, Darmstadt (DE)

( * ) Notice: Subject to any disclaimer, the term of this patent is extended or adjusted under 35 U.S.C. 154(b) by 265 days.

This patent is subject to a terminal disclaimer.

(21) Appl. No.: 10/585,031

(22) PCT Filed: Oct. 26, 2004

(86) PCT No.: PCT/EP2004/012078

§ 371 (c)(1),
(2), (4) Date: Jun. 29, 2006

(87) PCT Pub. No.: WO2005/075574

PCT Pub. Date: Aug. 18, 2005

(65) Prior Publication Data

US 2007/0151046 A1 Jul. 5, 2007

(30) Foreign Application Priority Data

Feb. 7, 2004 (DE) ............. 10 2004 006 142

(51) Int. Cl.
*A61Q 5/10* (2006.01)
*C07D 209/56* (2006.01)

(52) U.S. Cl. ............... 8/406; 548/437; 546/99
(58) Field of Classification Search ........... 546/99; 548/437; 8/406
See application file for complete search history.

(56) References Cited

U.S. PATENT DOCUMENTS

| 2,006,017 | A | 6/1935 | Exkert et al. |
| 5,292,881 | A | 3/1994 | Berneth et al. |
| 5,886,183 | A | 3/1999 | Langhals et al. |

FOREIGN PATENT DOCUMENTS

| DE | 887 198 | 8/1953 |
| DE | 953 064 | 11/1956 |
| DE | 2 236 55 | 2/1974 |
| EP | 0 769 532 | 4/1997 |
| EP | 1 464 328 | 10/2004 |
| FR | 2 853 231 | 10/2004 |
| GB | 962 019 | 6/1964 |
| GB | 973 260 | 10/1964 |
| WO | 02/066562 | 8/2002 |

OTHER PUBLICATIONS

Shibata et al., 2003, CAS: 138:385301.*
Schefczik's, 1976, CAS: 84:107077.*
Georgieva et al., 1974, CAS: 81:62718.*
H. Langshals: "Tetracarbonsaeurebisimid-Lactam . . . ", Angew. Chem., 1995, 107, No. 20, pp. 2436-2439.
Langhals, H., et al: "Tetracarboxylic Bisimide . . ." Angew. Chem. Int. Ed. Engl., 1995, 34, pp. 2234-2236 (In English).
Plakidin et al: "Derivatives of . . . " J. Org/ Chem. USSR, 1983, pp. 2273-2281 (In English).
Orzeszko et al: "Investigation of the . . . " Z. Naturforsch, 56B, 2001, pp. 1035-1040 (in English).
Lethao et al: "Photoinduced Electron Transfer in . . . " J. Phys. Chem. A, 104, 2000, pp. 6778-6785. (in English).
Stoll et al: "Ueber Derivate Des . . . " Helv. Chim. Acta, 41, 1951, pp. 382-396.
Wojciechowski et al: "Effect of Amide . . . " Polish J. Chem., 60, 1986, pp. 797-810 (in English).
Wendelin et al: "Fluorescence Reagents" J. Heterocyclic Chem, 24, 1987, pp. 1381-1390 (in English).
Gabbay et al: "Topography of Nucleic Acid . . . " Biochem Biophys. Res. Comm., vol. 51, No. 4., 1973, pp. 1083-1089 (in English).
Biadasz et al: "Langmuir Films of . . . " Dyes and Pigments, vol. 56, 2003, pp. 209-217 (in English).
Brana et al: "Synthesis and Cytostatic Activity . . . " Eur. J. Med. Chem., vol. 16, No. 3, 1981, pp. 207-212 (in English).
Pourjavadi et al: "Selective Preparations of . . . " J. Chem. Res. (S), 2001, pp. 485-487 (in English).
Rice et al: "Imidothiazoles" J. Med. Chem., vol. 11, No. 1, 1968, pp. 183-185 (in English).

* cited by examiner

*Primary Examiner*—Rei-tsang Shiao
(74) *Attorney, Agent, or Firm*—Michael J. Striker

(57) ABSTRACT

The present invention has for an object novel naphthalene dyes of formula (I) and colorants for keratin fibers, particularly human hair, containing these compounds.

(I)

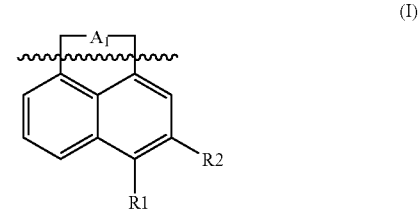

8 Claims, No Drawings

NEUTRAL AND CATIONIC NAPHTHALENE AND COLORANTS FOR KERATIN FIBERS CONTAINING THESE COMPOUNDS

CROSS-REFERENCE TO RELATED APPLICATIONS

This is the US National Stage of PCT/EP 04/12078, filed on 29 Jun. 2006, claims the priority under 35 U.S.C. 119(a)-(d) to German Patent Application No. 10 2004 006 142.4, filed 7 Feb. 2004.

This application is a 371 of PCT/EP04/12078 filed on Oct. 26, 2004.

The present invention has for an object novel uncharged and cationic naphthalene dyes and colorants for keratin fibers, for example human hair, containing these compounds.

In general, fibrous materials, particularly keratin-containing fibers, for example hair, wool or furs, are dyed either with oxidation dyes formed by oxidative coupling of one or more developer components with one or more coupler components, or with direct dyes. If needed, oxidation-resistant direct dyes can be added to the oxidative system to achieve special coloring effects. The direct dyes are incorporated into suitable carrier compositions and are then applied to the fibers. This method, generally known as tinting, is simple to apply, extremely gentle and, because it does not require the use of ammonia or peroxide, stands out by the fact that its damaging effect on the fibers is only slight. The dyes used for this purpose, however, must meet a few requirements. Thus, they must be toxicologically and dermatologically unobjectionable and must make it possible to achieve colorations of the desired intensity and brilliance. In addition, they must be resistant to washing, light, perspiration, pemanent waving, acids, bases and rubbing. In any event, such hair colorations must remain stable for at least four to six weeks under currently prevailing everyday conditions.

As a rule, for a direct, nonoxidative dye for keratin fibers, a combination of different nonoxidative dyes is needed to achieve certain color shades. Because the availability of yellow, red and blue dyes that adequately meet all requirements is limited, a great need still exists for such dyes. Another very interesting application of direct dyes is their use in agents for simultaneous brightening and dyeing. In these coloring compositions which can contain a higher amount of oxidants, the dyes used are subject to even more stringent requirements particularly as regards sufficient resistance to the oxidants used.

To date there hardly exist any dyes that meet the afore-said requirements and at the same time give a satisfactory coloring result. The purpose of the present invention therefore is to provide direct dyes for dyeing keratin fibers, particulary human hair, that meet these requirements.

Surprisingly, we have now found that certain novel naphthalene derivatives of general formula (I) can be used as direct dyes both in dye compositions without oxidants and in brightening dye compositions with a higher peroxide and/or persullfate content. In addition, the colorants containing the dyes of the invention are superior to common colorants in terms of their coloring properties.

The present invention therefore has for an object naphthalene derivatives of general formula (I)

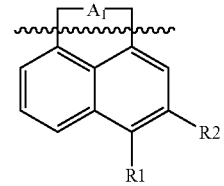

(I)

wherein
$A_1$ represents a partial structure of formulas (II), (III), IV), (V) and (VI)

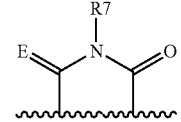

(II)

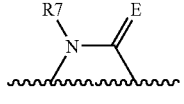

(III)

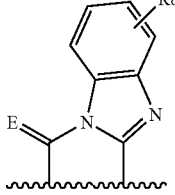

(IV)

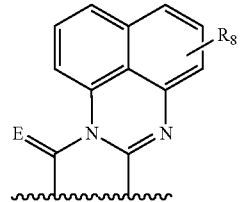

(V)

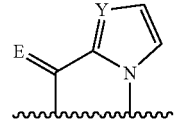

(VI)

E stands for oxygen or a sulfur atom;
Y stands for a nitrogen atom or (preferably) a quaternary nitrogen atom substituted with branched or linear $C_1$-$C_6$-alkyl groups, branched or linear $C_2$-$C_4$-hydroxyalkyl groups or branched or linear $C_4$-$C_6$-polyhydroxyalkyl groups;
$R_1$ and $R_2$ independently of each other stand for hydrogen, an —N—$R_3R_4$ group, a nitro group, an —N=N—$R_5$ group or an —N=C—$R_3R_6$ group;
$R_3$ and $R_4$ can be equal or different and stand for hydrogen, a $C_1$-$C_6$-alkylamino group, $C_1$-$C_6$-N,N-dialkylamino group, $C_1$-$C_6$-alkylcyano group, methoxymethyl group, tert. butyl group, isopropyl group, $C_1$-$C_6$-alkyl group, $C_1$-$C_6$-alkyloxy group, $C_1$-$C_6$-hydroxyalkyl group, $C_1$-$C_6$-alkylcarboxylic acid group, $C_1$-$C_6$-alkylcarboxylate ester group, $C_1$-$C_6$-alkylcarboxamide group, C₁-C₆-alkylsulfonic acid group, C₁-C₆-alkylsulfonate ester group, C₁-C₆-alkylsulfonamide group, phenyl group or -(L)-B⁺ group;

R₅ stands for a group of formula (VII) or (VIII), the group of formula (VIII) being particularly preferred

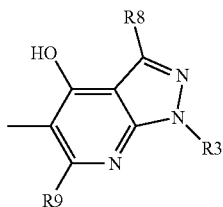
(VII)

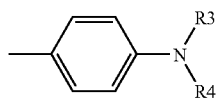
(VIII)

R₆ stands for a compound of formula (IX), (X) or (XI);

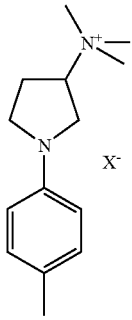

(IX)

(X)

(XI)

R₇ stands for a hydrogen atom, an aliphatic C₁-C₆-alkyl group that can be linear or branched, unsubstituted or substituted with one or more hydroxyl groups or cationic groups of the B⁺ type; an aromatic group of general formula (XII) or (XIII)

(XII)

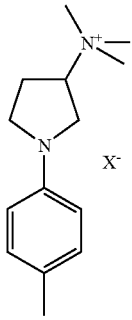

(XIII)

or a five-membered or six-membered heterocycle or (preferably) a bicyclic heterocyclic compound of general formula (XIV), (XV), (XVI) or (XVII);

(XIV)

(XV)

(XVI)

(XVII)

R₈ and R₉ can be equal or different and denote hydrogen, an amino group, a (C₁-C₆)-alkylamino group, a (C₁-C₆)-N,N-dialkylamino group, a (C₁-C₆)-N,N-(dihydroxyalkyl) amino group, fluorine, chlorine, bromine, iodine, a cyano group, a (C₁-C₆)-alkylcyano group, a methoxymethyl group, a tert. butyl group, an isopropyl group, a (C₁-C₆)-alkyl group, a (C₁-C₆)-alkyloxy group, C₁-C₆-hydroxyalkyl group, (C₁-C₆)-hydroxyalkyloxy group, C₁-C₆-alkylcarboxylic acid group, C₁-C₆-alkylcarboxylate ester group, C₁-C₆-alkylcarboxamide group, C₁-C₆-alkylsulfonic acid group, C₁-C₆-alkylsulfonate ester group, C₁-C₆-alkylsulfonamide group, phenyl group, sulfonic acid group or -(L)-B⁺ group;

L stands for a (C₁-C₆)-alkylene group;

B⁺ stands for an aromatic, heterocyclic quaternary ammonium compound—preferably a quaternary compound of N-methylimidazole, N-allylimidazole, 2-ethylimidazole, 1,2-dimethylimidazole; pyridine, 4-dimethylaminopyridine, pyrimidine, pyrazole, N-methylpyrazole or quinoline; a nonaromatic heterocyclic quaternary ammonium compound—particularly a quaternary compound of N-methylmorpholine, N-ethylmorpholine or 1-methylpiperidine; a quaternary alkylammonium or arylammonium compound of formula $NR_aR_bR_c$ wherein $R_a$, $R_b$ and $R_c$ independently of each other denote a benzyl group, phenyl group or ($C_1$-$C_6$)-alkyl group—particularly a methyl, ethyl, propyl, isopropyl or butyl group, and the aforesaid alkyl groups possibly are unsubstituted or substituted with one or more hydroxyl groups or amino groups; or a quaternary phosphonium group, for example a tributylphosphonium group, but particularly a trimethylammonium group or triethylammonium group, and $X^-$ denotes an anion, preferably a sulfate, phosphate, hydrogen phosphate, oxalate, formate, acetate, citrate, tartrate, malonate, pyruvate, chloride, bromide, iodide or methylsulfate anion, the chloride anion, bromide anion and methylsulfate anion being particularly preferred.

Suitable neutral or cationic direct dyes of general formula (I) are, for example: 3-((E)-{4-[ethyl(2-hydroxyethyl)amino]phenyl}diazenyl)-8-methyl-7-keto-7H-benzo[de]imidazo[1,2-a]quinolin-8-ium methylsulfate, 3-{(E)-[4-hydroxy-1-(2-hydroxyethyl)-3,6-dimethyl-1H-pyrazolo[3,4-b]pyridin-5-yl]diazenyl}-8-methyl-7-keto-7H-benzo[de]imidazo[1,2-a]quinolin-8-ium methylsulfate, 3-methyl-2-{5-nitro-2-ketobenzo[cd]indol-1(2H)-yl}-1,3-benzothiazol-3-ium methylsulfate, 3-nitro-7H-benzo[de]-imidazo[1,2-a]quinolin-7-one, 2-{5-(dimethylamino)-2-ketobenzo[cd]indol-1(2H)-yl}-3-methyl-1,3-benzothiazol-3-ium methylsulfate, 3-{2-[4-(5-(dimethylamino)-1,3-diketo-1H-benzo[de]isoquinolin-2(3H)-yl)(ethyl)anilino]ethyl}-1-methyl-1H-imidazol-3-ium bromide, 5-((E)-{1-[4-(dimethylamino)-phenyl]-2-keto-1,2-dihydrobenzo[cd]indol-6-yl}diazenyl)4-hydroxy-1-(2-hydroxyethyl)-3,6,7-trimethyl-1H-pyrazolo[3,4-b]pyridin-7-ium methylsulfate, 3-(dimethylamino)-8-methyl-7-keto-7H-benzo[de]-imidazo[1,2-a]quinolin-8-ium methylsulfate, 1-{4-[bis(hydroxyethyl)amino]phenyl}-6-nitro-benzo[cd]-indol-2(1H)-one, 3-{2-[ethyl4-(6-nitro-2-ketobenzo[cd]indol-1(2H)-yl)anilino]ethyl}-1-methyl-1H-imidazol-3-ium bromide, 4-((E)-{[2-(3,4-dimethoxyphenyl)-1,3-diketo-2,3-dihydro-1H-benzo[de]isoquinolin-6-yl]imino}methyl)-1-(2-hydroxyethylpyridinium bromide, 2-(3,4-dimethoxyphenyl)-6-nitro-1H-benzo[de]isoquinolin-1,3-(2H)-dione, 1,(3,4-dimethoxyphenyl)-6-nitrobenzo[cd]indol-2(1H)-one, 1-methyl-3-[2-({2-[((2Z)-3-methyl-1,3-benzothiazol-2(3H)ylidene)amino]-1,3-diketo-2,3-dihydro-1H-benzo[de]isoquinolin-6-yl}amino)ethyl]-1H-imidazol-3-ium bromide, 1-(2-hydroxyethyl)-4-{(E)-[(7-keto-7H-benzimidazo[2,1-a]benzo[de]isoquinolin-2-yl)imino]methyl}pyridinium bromide, 1-(2-hydroxyethyl4-{(E)-[7-thioxo-7H-benzimidazo[2,1-a]benzo[de]isoquinolin-2-yl)imino]methyl}pyridinium bromide, 2-{ethyl4-[(E)-14-keto-14H-benzo[4,5]isoquinolino[2,1-a]perimidin-9-yl)diazenyl]anilino}-N,N,N-trimethylethylethanaminium bromide, 2-{ethyl4-[(E)-7-keto-7H-benzimidazo-[2,1-a]benzo[de]isoquinolin-2-yl)diazenyl]anilino}-N,N,N-trimethylethylethanaminium bromide, 2-{ethyl-4-[(E)-(7-thioxo-7H-benzimidazo[2,1-a]benzo[de]isoquinolin-2-yl)diazenyl]anilino}-N,N,N-trimethylethanaminium bromide, 2-{4-[(E)-(1,3-diketo-2,3-dihydro-1H-benzo[de]isoquinolin-6-yl)diazenyl](ethyl)anilino}-N,N,N-trimethylethanaminium bromide, 1-(2-hydroxyethyl)-4-[(E)-({2-[((2Z)-3-methyl-1,3-benzothiazol-2(3H)-ylidene)amino]-1,3-diketo-2,3-dihydro-1H-benzo[de]-isoquinolin-5-yl}imino)methyl]pyridinium bromide, 4-{(E)-[(1,3-diketo-2,3-dihydro-1H-benzo[de]-isoquinolin-6-yl)-imino]methyl}-1-(2-hydroxyethyl)pyridinium bromide, 2-[4-((E)-{1-[4-(dimethylamino)phenyl]-2-ke-to-1,2-dihydrobenzo[cd]indol-5-yl}diazenyl)(ethyl)anilino]-N,N,N-trimethylethanaminium bromide, 3-{2-[ethyl4-(2-keto-5-((E)-{3,4,6-trimethyl-1-[2-(1-methyl-1H-imidazol-3-ium-3-yl)ethyl-1H-pyrazolo[3,4-b]pyridin-5-yl}diazenyl)benzo[cd]indol-1(2H)-yl)anilino]ethyl}-1-methyl-1H-imidazol-3-ium dibromide, 1-(2-hydroxyethyl) 4-[(E)({2-[((2Z)-3-methyl-1,3-benzothiazol-2(3H)-ylidene)amino]-1,3-diketo-2,3-dihydro-1H-benzo[de]isoquinolin-6-yl}imino)methyl]pyridinium bromide, 2-{6-(dimethylamino)-1,3-diketo-1H-benzo[de]isoquinolin-2(3H)-yl}-3,4,5-trimethyl-1,3-thiazol-3-ium methylsulfate, 2-{5-(dimethylamino)-2-ketobenzo[cd]indol-1(2H)-yl}-3,4,5-trimethyl-1,3-thiazol-3-ium methylsulfate, 3-{2-[ethyl4-(6-nitro-1,3-diketo-1H-benzo-[de]isoquinolin-2(3H)-yl)anilino]ethyl}-1-methyl-1H-imidazol-3-ium bromide, 3-{2-[5-methoxy-2-(6-nitro-1,3-diketo-1H-benzo-[de]isoquinolin-2(3H)-yl)anilino]ethyl}-1-methyl-1H-imidazol-3-ium bromide, 2-[(3-methyl-1,3-benzothiazol-2-(3H)-ylidene)amino]-6-nitro-1H-benzo[de]isoquinolin-1,3(2-(1,3-benzothiazol-2-yl) -6-nitro-1H-benzo-[de]isoquinolin-1,3-(2H)-dione, 1-(2-hydroxyethyl)-4{(E)-[14-keto-14H-benzo[4,5]-isoquino[2,1-a]-perimidin-9-yl)imino]methyl}pyridinium bromide and 2-{2-[(2-hydroxyethyl)amino]-4-methoxyphenyl}-5-nitro-1H-benzo[de]isoquinolin-1,3(2H)-dione.

Preferred compounds of general formula (I) are 3-((E) -{4-[ethyl(2-hydroxyethyl)amino]phenyl}diazenyl)-8-methyl-7-keto-7H-benzo[de]imidazo-[1,2-a]quinolin-8-ium methylsulfate, 3-{(E)-[4-hydroxy-1-(2-hydroxyethyl)-3,6-dimethyl-1H-pyrazolo[3,4-b]pyridin-5-yl]diazenyl}-8-methyl-7-keto-7H-benzo[de]-imidazo[1,2-a]quinolin-8-ium methylsulfate, 3-methyl-2-{5-nitro-2-ketobenzo[cd]-indol-1(2H)-yl}-1,3-benzothiazol-3-ium methylsulfate, 2-{5-(dimethylamino)-2-ketobenzo[cd]indol-1-(2H)-yl}-3-methyl-1, 3-benzothiazol-3-ium methylsulfate, 5-((E)-{1-[4-(dimethylamino)phenyl]-2-keto-1,2-dihydrobenzo[cd]indol-6-yl}diazenyl)-4-hydroxy-1-(2-hydroxyethyl)-3,6,7-trimethyl-1H-pyrazolo[3,4-b]pyridin-7-ium methylsulfate, 1-{4-[bis(hydroxyethyl)amino]phenyl}-6-nitrobenzo[cd]indol-2(1H)-one, 3-{2-[ethyl-4-(6-nitro-2-ketobenzo[cd]indol-1(2H)-yl)anilino]ethyl}-1-methyl-1H-imidazol-3-ium bromide, 1-(2-hydroxyethyl)-4-{(E)-[(7-keto-7H-benzimidazo[2,1-a]benzo[de]isoquinolin-2-yl)imino]methyl}pyridinium bromide, 4-{(E)-[(1,3-diketo-2,3-dihydro-1H-benzo[de]isoquinolin-6-yl)imino]methyl}-1-(2-hydroxyethyl)pyridinium bromide, 2-[4-((E)-{1-[4-(dimethylamino)phenyl]-2-keto-1,2-dihydrobenzo[cd]indol-5-yl}diazenyl)(ethyl)anilino]-N,N,N-trimethylethanaminium bromide, 2-[(3-methyl-1,3-benzothiazol-2(3H)-ylidene)amino]-6-nitro-1H-benzo[de]isoquinolin-1,3-(2H)-dione, 2-(1,3-benzothiazol-2-yl)-6-nitro-1H-benzo[de]isoquinolin-1,3(2H)-dione, 1-(2-hydroxyethyl-4-{(E)-[(14-keto-14H-benzo[4,5]isoquino-[2,1-a]perimidin-9-yl)imino]methyl}pyridinium bromide and 2-{2-[(2-hydroxyethyl)amino]-4-methoxyphenyl}-5-nitro-1H-benzo[de]isoquinolin-1,3-(2H)-dione.

The naphthalene derivatives of general formula (I) of the invention can be obtained by known methods of synthesis from commercially available or readily prepared components.

Suitable as naphthalene precursors of formula (XVIII) are, for example, the following anhydrides:
4-nitronaphthalene-1,8-dicarboxylic anhydride and
3-nitronaphthalene-1,8-dicarboxylic anhydride.

By a condensation reaction according to Scheme 1 at elevated temperature in a suitable solvent, or example glacial acetic acid, DMF or molten imidazole, it is possible to prepare from the naphthalene-1,8-dicarboxylic anhydride of formula (XVIII) and a primary aliphatic, aromatic or heterocyclic amine or hydrazone (A1) the corresponding unsymmterically substituted imide, amidine or isoamidine.

According to H. Langhals et al. (Angew. Chem. 1995, 107; 2436-2439; Angew. Chem., Int. Ed. Engl. 1995 34, 2234-2236) and EP 0 769 532 A1, lactams (XX) can be prepared from any desired diimide derivative (XIX) by a ring-contraction reaction in a DMSO/methanol mixture under strongly alkaline conditions (Scheme 2)

Scheme 1:

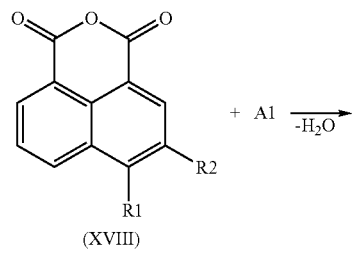

(XVIII)

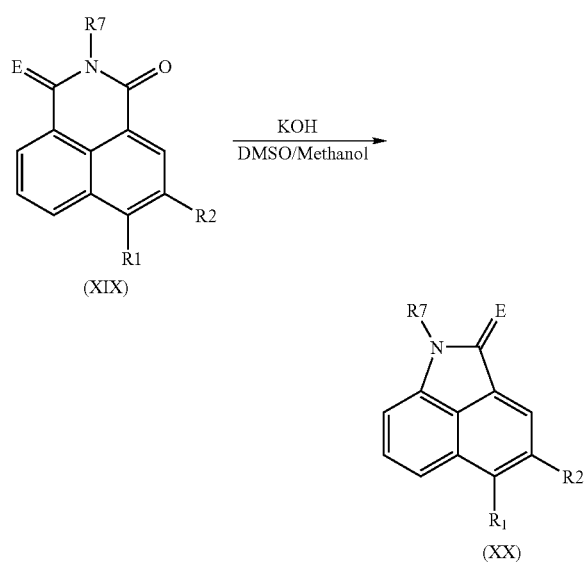

Scheme 2:

(XIX)

(XX)

The cationic representatives can be prepared in simple manner either by introducing a cationic group (Scheme 3) or by quaternization of heterocyclic nitrogen atoms (Scheme 4).

Scheme 3

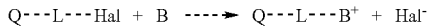

Q---L---Hal + B ----► Q---L---B$^+$ + Hal$^-$

According to Scheme 3, compounds of general formula Q-L-Hal, wherein the Q group stands for a neutral naphthalene derivative of formula (I) and L stands for $C_1$-$C_6$-alkyl (Hal stands for chlorine, bromine or iodine), are made to undergo nucleophilic substitution with compounds of type B in a dipolar aprotic solvent with B denoting an aromatic heterocyclic compound—preferably an N-methylimidazole, N-allylimidazole, 2-ethylimidazole or 1,2-dimethylimidazole, pyridine, 4-dimethylaminopyridine, pyrimidine, pyrazole, N-methylpyrazole or quinoline; or a nonaromatic heterocyclic compound—particularly N-methylmorpholine, N-ethylmorpholine or 1-methylpiperidine; or an alkyl—or aryl compound of formula $NR_aR_bR_c$, wherein $R_a$, $R_b$ and $R_c$ have the afore-indicated meaning and denote, for example, a trimethylamino group, triethylamino group or tributylamino group; or a tertiary phosphor-organic group ("tertiary phosphine").

Scheme 4

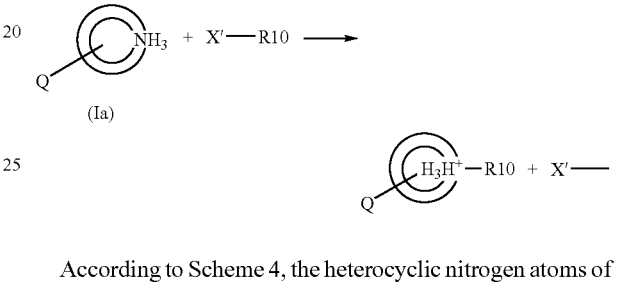

(Ia)

According to Scheme 4, the heterocyclic nitrogen atoms of the neutral naphthalene derivatives of formula (Ia) are quaternized with an alkylating agent of general formula X'—$R_{10}$ wherein X' stands for chlorine, bromine, iodine or methylsulfate and $R_{10}$ stands for a $C_1$-$C_6$-alkyl group, $C_1$-$C_3$-hydroxyalkyl group or $C_4$-$C_6$-polyhydroxyalkyl group.

The novel naphthalene derivatives of general formula (I) make it possible to obtain a uniform, intense and brilliant coloration on fibers, particularly keratin fibers, for example human hair, wool and furs, under gentle conditions tolerated by skin, the colorations showing unusually high resistance to light, perspiration and shampooing. Moreover, with special excitation, for example with UV light, it is possible to observe in some cases pronounced solid-body fluorescence of the dyed fibers.

The invention therefore also has for an object (a) an agent for coloring keratin fibers, particularly human hair, and (b) an agent containing an oxidant for the simultaneous brightening and coloring of keratin fibers, particularly human hair, characterized in that said agent contains at least one naphthalene derivative of general formula (I).

The colorants of the invention contain the naphthalene derivatives of general formula (I) preferably in an amount from 0.01 to 10 weight percent and particularly from 0.1 to 8 weight percent.

Besides the dyes of general formula (I), the colorant (a) of the invention can additionally contain other known direct dyes selected from the group consisting of nitro dyes, azo dyes, anthraquinone dyes and triphenylmethane dyes, alone or in admixture with one another, for example:
1,4-bis-[(2-hydroxyethyl)amino]-2-nitrobenzene, 1-(2-hydroxyethyl)amino-2-nitro-4-[di(2-hydroxyethyl)amino] benzene (HC Blue No. 2), 1-amino-3-methyl4-[(2-hydroxyethyl)amino]-6-nitrobenzene (HC Violet No. 1), 4-[ethyl-(2-hydroxyethyl)amino]-1[(2-hydroxyethyl) amino]-2-nitrobenzene hydrochloride (HC Blue No. 12), 1-[(2,3-dihydroxypropyl)amino]4-[methyl-(2-hydroxyethyl)amino]-2-nitrobenzene (HC Blue No. 10), 1-[(2,3-dihydroxypropyl)amino]-4-[ethyl-(2-hydroxyethyl)- amino]-2-nitrobenzene hydrochloride (HC Blue No. 9), 1-(3-hydroxypropylamino)-4-[di(2-hydroxyethyl) amino]-2-nitrobenzene (HC Violet No. 2), 1-amino-4-[(2-hydroxyethyl)amino]-2-nitrobenzene (HC Red No. 7), 2-amino4,6-dinitrophenol, 1,4-diamino-2-nitrobenzene (CI 76070), 4-amino-2-nitrodiphenylamine (HC Red No. 1), 1-amino4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-2-nitro-1-[(prop-2-en-1-yl)amino]benzene, 4-amino-3-nitrophenol, 4-[(2-hydroxyethyl)amino]-3-nitrophenol, 4-[(2-nitrophenyl)amino]phenol (HC Orange No. 1), 1-[(2-aminoethyl)amino]4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1, 4-[di(2,3-dihydroxypropyl)amino]-2-nitrobenzene (HC Red No. 11), 2-[(2-hydroxyethyl)amino]4,6-dinitrophenol, 4-ethylamino-3-nitrobenzoic acid, 2-[(4-amino-2-nitrophenyl)-amino]benzoic acid, 2-chloro-6-ethylamino4-nitrophenol, 2-amino-6-chloro-4-nitrophenol, 4-[(3-hydroxypropyl)amino]-3-nitrophenol, 2,5-diamino-6-nitropyridine, 3-amino-6-(methylamino)-2-nitropyridine, 1,2,3,4-tetrahydro-6-nitroquinoxaline, 7-amino-3,4-dihydro-6-nitro-2H-1,4-benzoxazine (HC Red No. 14), 1,2-diamino-4-nitrobenzene (CI 76020), 1-amino-2-[(2-hydroxyethyl)-amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl) amino]-2-nitrobenzene (HC Yellow No. 2), 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)-amino]-4-nitrobenzene, 4-[(2,3-dihydroxypropyl)amino]-3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl) amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl) amino]-3-nitrobenzamide (HC Yellow No. 15), 2,4-dinitro-1-hydroxynaphthalene; 1,4-di-[(2,3-dihydroxypropyl) amino]-9,10-anthraquinone, 1,4-di[(2-hydroxyethyl) amino]-9,10-anthraquinone (CI 61545, Disperse Blue 23), 1-amino-4-hydroxy-9,10-anthraquinone (CI 60710, Disperse Red 15), 1-hydroxy-4-[(4-methyl-2-sulfophenyl) amino]-9,10-anthraquinone, 7-beta-D-glucopyranosyl-9, 10-dihydro-1-methyl-9,10-diketo-3,5,6,8-tetrahydroxy-2-anthracenecarboxylic acid (CI 75470, Natural Red 4), 1-[(3-aminopropyl)amino]-9,10-anthraquinone (HC Red No. 8), 1,4-diamino-9,10-anthraquinone (CI 61100, Disperse Violet No. 1), 1-amino-4-(methylamino)-9,10-anthraquinone (CI 61105, Disperse Violet No. 4, Solvent Violet No. 12), N-(6-{[3-chloro-4-(methylamino)phenyl] imino}-4-methyl-3-keto-1,4-cyclohexadien-1-yl)urea (HC Red No. 9), 2-((4-(di(2-hydroxyethyl)-amino)phenyl) amino)-5-((2-hydroxyethyl)amino)-2,5-cyclohexadien-1, 4-dione (HC Green No. 1), 2-hydroxy-1,4-naphthoquinone (CI 75480, Natural Orange No. 6), 1,2-dihydro-2-(1,3-dihydro-3-keto-2H-indol-2-ylidene)-3H-indol-3-one (CI 73000), 1,3-bis-(dicyanomethylene)indane; di[4-(diethylamino)phenyl][4-(ethylamino)naphthyl]carbenium chloride (CI 42595; Basic Blue No. 7), di[4-(dimethylamino)phenyl][4-(phenylamino)naphthyl]carbenium chloride (CI 44045, Basic Blue No. 26), Basic Blue No. 77, 8-amino-2-bromo-5-hydroxy4-imino-6-[(3-(trimethylammonio)phenyl)amino]-1(4H)-naphthalinone chloride (CI 56059, Basic Blue No. 99), tri(4-amino-3-methylphenyl) carbenium chloride (CI 42520, Basic Violet No. 2), di(4-aminophenyl)(4-amino-3-methylphenyl)carbenium chloride (CI 42510, Basic Violet No. 14), 1-[(4-aminophenyl) azo]-7-(trimethylammonio)-2-naphthol chloride (CI 12250. Basic Brown No.16), 3-[(4-amino-2,5-dimethoxyphenyl)azo]-N,N,N-trimethylbenzenaminium chloride (CI 112605, Basic Orange No. 69), 1-[(4-amino-2-nitrophenyl)azo]-7-(trimethylammonio)-2-naphthol chloride (Basic Brown No. 17), 1-[(4-amino-3-nitrophenyl)azo]-7-(trimethylammonio)-2-naphthol chloride (CI 12251, Basic Brown No. 17) [sic], 2-[(4-aminophenyl)azo]-1,3-dimethyl-1H-imidazol-3-ium chloride (Basic Orange No. 31), 3,7-diamino-2,8-dimethyl-5-phenylphenazinium chloride (CI 50240, Basic Red No. 2), 1,4-dimethyl-5-{[4-(dimethylamino)phenyl]azo}-1,2,4-triazolium chloride (CI 11055, Basic Red No. 22),1,3-dimethyl-2-[(4-dimethylamino)phenyl]azo-1H-imidazol-3-ium chloride (Basic Red No. 51), 2-hydroxy-1-[(2-methoxyphenyl)azo]-7-(trimethylammonio)naphthalene chloride (CI 12245, Basic Red No. 76), 3-methyl-1-phenyl-4-{[3-(trimethylammonio)phenyl]azo}pyrazol-5-one chloride (CI 12719, Basic Yellow No. 57), 1-methyl4-[(methylphenylhydrazono) methyl]pyridinium methylsulfate (Basic Yellow No. 87), 1-(2-morpholiniumpropylamino)-4-hydroxy-9,10-anthraquinone methylsulfate, 1-{[3-(dimethylpropylaminium)propyl]amino}-4-(methylamino)-9,10-anthraquinone chloride, 1-[di(2-hydroxyethyl)amino]-3-methyl-4-[(4-nitrophenyl)azo]benzene (CI 11210, Disperse Red No. 17),1-[di(2-hydroxyethyl)amino]-4-[(4-nitrophenyl)azo]benzene (Disperse Black No. 9), 4-[(4-aminophenyl)azo]-1-[di(2-hydroxyethyl)amino]-3-methylbenzene (HC Yellow No. 7), 2,6-diamino-3-[(pyridin-3-yl)azo]pyridine and 2-((4-(ethyl(2-hydroxyethyl)amino)-2-methylphenyl)azo)-5-nitro-1,3-thiazole (CI 111935, Disperse Blue No. 106).

Besides the dyes of general formula (I), the colorant (b) of the invention which additionally contains an oxidant and particularly hydrogen peroxide or a hydrogen peroxide adduct (for example sodium percarbonate or urea peroxide) and/or a persulfate (for example ammonium persulfate, sodium persulfate or potassium persulfate) and/or a perborate, can also contain other known direct dyes resistant to oxidants, for example:

3-(2',6'-diaminopyridyl-3'-azo)pyridine(=2,6-diamino-3-((pyridin-3-yl)azo)pyridine), 2-((4-ethyl(2-hydroxyethyl) amino)-2-methylphenyl)azo)-5-nitro-1,3-thiazole (Disperse Blue 106), N,N-di(2-hydroxyethyl)-3-methyl4-((4-nitrophenyl)azo)aniline (Disperse Red 17, CI 11210), 3-diethylamino-7-(4-dimethylaminophenylazo)-5-phenylphenazinium chloride (CI 11050), 4-(2-thiazolylazo) resorcinol, 4-[(4-phenylamino)azo]benzenesulfonic acid sodium salt (Orange IV), 1-[(3-aminopropyl)amino]-9,10-anthracenedione (HC Red No. 8), 3',3",4,5,5',5",6,7-octabromophenolsulfonphthalein (Tetrabromophenol Blue), 1-[(4-amino-3,5-dimethylphenyl)-(2,6-dichlorophenyl) methylene]-3,5-dimethyl-4-imino-2,5-cyclohexadiene phosphoric acid (1:1) (Basic Blue 77), 3',3",5',5"-tetrabromo-m-cresolsulfonphthalein, 2,4-dinitro-1-naphthol- 7-sulfonic acid disodium salt (Acid Yellow 1, CI 10316), 4-[(2'-hydroxy-1-naphthyl)azo]benzenesulfonic acid sodium salt (Acid Orange 7, CI 15510), 3',6'-dihydroxy-2', 4',5',7'-tetraiodispiro[isobenzofuran-1(3H),9'(9H)xanthen]-3-one disodium salt (Acid Red 51, CI 45430), 6-hydroxy-5-[(2-methoxy-5-methyl4-sulfophenyl)azo]-2-naphthalenesulfonic acid disodium salt (FD&C Red No. 40, CI 16035), 2,4-dinitro-1-naphthol sodium salt (Acid Yellow 24, CI 10315), 2',4',5',7'-tetrabromo-4,5,6,7-tetrachloro-3',6'-dihydroxyspiro[isobenzofuran-1(3H),9'(9H) xanthen]-3-one disodium salt (Acid Red 92, CI 45410), 4-(2-hydroxy-1-naphthylazo)-3-methylbenzenesulfonic acid sodium salt (Acid Orange 8, CI 15575), 2-amino-1,4-naphthalenedione, dithizone(1,5-diphenylthiocarbazone), N-(2-hydroxyethyl)-2-nitro-4-trifluoromethyl)aniline (HC Yellow 13), N-(2-hydroxyethyl)-4-nitroaniline and 4-chloro-N-(2,3-dihydroxypropyl)-2-nitroaniline.

The agent of the invention can contain the afore-said additional direct dyes in a total amount of about 0.01 to 4 weight percent, the total amount of dyes in the colorant of the invention preferably being about 0.01 to 10 weight percent and particularly 0.1 to 5 weight percent.

Furthermore, the colorant of the invention can contain all common additives known to be used in such preparations, for example perfume oils, complexing agents, waxes, preservatives, thickeners, alginates, guar gum, hair-care substances, for example cationic polymers or lanolin derivatives, or anionic, nonionic, amphoteric or cationic surface-active substances. Preferably used are amphoteric or nonionic surface-active substances, for example betaine surfactants, propionates and glycinates, for example cocoamphoglycinates or cocoamphodiglycinates, ethoxylated surfactants with 1 to 1000 ethylene oxide units and preferably with 1 to 300 ethylene oxide units, for example glyceride alkoxylates, for example with 25 ethylene oxide units, ethoxylated castor oil, polyethylene glycol amides, ethoxylated alcohols and ethoxylated fatty alcohols (fatty alcohol alkoxylates) and ethoxylated sugar esters of fatty acids, particularly ethoxylated sorbitan fatty acid esters. The afore-said constituents are used in amounts commonly employed for such purposes, for example the surface-active substances at a concentration from 0.1 to 30 weight percent, and the hair-care agents in an amount from 0.1 to 5 weight percent. The colorant of the invention, particularly when it is a hair colorant, can be in the form of an aqueous or aqueous-alcoholic solution or a cream, gel, emulsion or aerosol foam. The hair colorant can be in the form of a one-component preparation or in the form of a multicomponent preparation, for example in the form of a two-component preparation in which the dye derivative of general formula (I) is packaged separately from the other constituents, and the ready-to-use hair colorant is prepared just before use by mixing the two components. When the dyes are to be used together with an oxidant, the colorant can also be packaged in the form of a 2-component preparation in which one component is the oxidant and the other component contains the other constituents, the oxidant optionally also consisting of several components (for example, 1. hydrogen peroxide and 2. persulfate).

The colorant of the invention has a pH of about 2 to 10, preferably of about 5 to 10 and particularly a neutral to basic pH of about 7 to 10. Both organic and inorganic acids and bases are suitable for pH ad-justment. Suitable acids are, in particular, α-hydroxycarboxylic acids, for example glycolic acid, lactic acid, tartaric acid, citric acid or malic acid, ascorbic acid, glucuronolactone, acetic acid, hydrochloric acid or phosphoric acid as well as mixtures of these acids. Suitable bases are, in particular, sodium carbonate, sodium hydrogen carbonate, alkanolamines, for example mono-ethanolamine or triethanolamine, ammonia, aminomethylpropanol and sodium hydroxide.

The colorant of the invention is normally used by applying to the fibers an amount thereof sufficient for the dyeing, usually about 30 to 120 grams (optionally with addition of a suitable oxidant).

The colorant is then allowed to act at about 15 to 45° C. for about 1 to 60 minutes and preferably for 5 to 30 minutes, after which the fibers are thoroughly rinsed with water, optionally washed with a shampoo and then dried.

Moreover, if no oxidant is added to the dye composition, the afore-described colorant can contain natural or synthetic polymers or modified polymers of natural origin commonly used in cosmetic agents whereby the hair is fixed at the same time as it is dyed. Such agents are generally referred to as tint fixatives or dye fixatives.

Synthetic polymers that are known to be used for this purpose in the cosmetic field are, for example, polyvinylpyrrolidone, polyvinyl acetate, polyvinyl alcohol or polyacrylate compounds such as polyacrylic acid or polymethacrylic acid, basic polymers of esters of polyacrylic acid, polymethacrylic acid and aminoalcohols, for example the salts or quaternization products thereof, polyacrylonitrile, polyvinyl acetate, as well as the copolymers of such compounds, for example polyvinylpyrrolidone-vinyl acetate, whereas suitable natural polymers or modified natural polymers are, for example, chitosan (deacetylated chitin) or chitosan derivatives.

The afore-said polymers can be contained in the colorant of the invention in amounts commonly employed for such cosmetic agents, particularly in an amount from about 1 to 5 weight percent. The pH of the tint fixative or dye fixative of the invention is preferably about 6 to 9.

The colorant additionally providing hair fixing is used in the known and usual manner by moistening the hair with the fixing agent, arranging (styling) the hair into a hairdo and then drying.

The colorant of the invention imparts to keratin fibers (for example human hair, wool or furs) an outstanding, uniform, intense and very durable coloration without appreciably staining the skin or the scalp, a coloration capable of withstanding five or more hair washings without an appreciable fading of the hair color.

The following examples will explain the subject matter of the invention in greater detail without limiting it to the examples.

EXAMPLES

Example 1

Preparation of 4-{(E)-[(1,3-diketo-2,3-dihydro-1H-benzo[de]isoquinolin-6-yl)imino]methyl}-1-(2-hydroxyethyl)pyridinium bromide Step 1: Preparation of 6{[(E)-4-pyridinylmethylidene] amino}-1H-benzo[de]isoquinolin-1,3-(2H)-dione 3 g (14.13 mmol) of 4-aminonaphthalene-1,8-dicarboximide and 7.56 g (70.65 mmol) of 4-pyridinecarboxaldehyde in 180 mL of a 2:1 mixture of concentrated sulfuric acid and glacial acetic acid were stirred at 80° C. for 2 hours. The mixture was then poured onto ice and slowly neutralized or adjusted to a slightly alkaline pH (pH=about 8) with NaOH. The resulting precipitate was suction-filtered off, washed with copious amounts of water and then dried under vacuum. Yield: 2.28 g (54% of the theoretical), lustrous yellow powder. $^1$H-NMR (d$_6$-DMSO/300 MHz): δ=6.46 (s, 1H); 7.52-7.56 (m, 2H, aromatic); 7.20 (d, J=5.7 Hz, 2H, pyridyl); 8.38 (m, 1H, aromatic); 8.65 (d, J=5.7 Hz, 2H, pyridyl), 8.71-8.73 (m, 2H, aromatic); 11.41 (s, 1 H, N—H).

Step 2: Preparation of 4-{(E)-[(1,3-diketo-2,3-dihydro-1H-benzo[de]isoquinolin-6-yl) imino]methyl}-1(2-hydroxyethyl)pyridinium bromide 2.34 g (18.75 mmol) of bromoethanol was added dropwise to a solution of 1.13 g (3.75 mmol) of 6-{[(E)-4-pyridinylmethylidene]amino}-1H-benzo[de]isoquinolin-1,3(2H)-dione in 60 mL of acetonitrile or acetone and the solution was then heated at reflux for 1 hour. After concentration to about ⅓ of the amount of solvent and cooling to room temperature, the resulting precipitate was suction-filtered off, washed with ethyl acetate and dried under vacuum. Yield: 0.59 g (37% of the theoretical), dark-yellow powder. $^1$H-NMR (d$_6$-DMSO/300 MHz): δ=3.58 (t, J=13.5 Hz, 2H, ethyl); 4.01 (t, J=13.5 Hz, 2H, ethyl); 6.45 (s, 1H); 7.54-7.58 (m, 2H, aromatic); 7.19 (d, J=5.8 Hz, 2H, pyridyl); 8.40 (m, 1H, aromatic); 8.63 (d, J=5.8 Hz, 2H, pyridyl); 8.72-8.75 (m, 2H, aromatic); 11.39 (s, 1H, N—H).

Example 2

Preparation of 3-{2-[ethyl-4-(6-nitro-1,3-diketo-1H-benzo[de]isoquinolin-2(3H)-yl)anilino]ethyl}-1-methyl-1H-imidazol-3-ium bromide Step 1: Preparation of 2-{4-[ethyl(2-hydroxyethyl)amino]phenyl}-6-nitro-1H-benzo[de]isoquinolin-1,3(2H)-dione 2.0 g (8.22 mmol) of 4-nitronaphthalene-1,8-dicarboxylic anhydride and 2.68 g (9.04 mmol) of N-ethyl-N-(2-hydroxyethyl)-p-phenylenediamine sulfate monohydrate were stirred in 12 g of molten imidazole at 130° C. under an argon atmosphere for 1 hour. After cooling, the mixture was poured into 400 mL of 2 N hydrochloric acid and the precipitate was suction-filtered off, washed with water and dried. The resulting product was used in Step 2 without further purification.

Step 2: Preparation of 2-{4-[(2-bromoethyl)(ethyl)amino]phenyl}-6-nitro-1H-benzo-[de]isoquinolin-1,3-(2H)-dione 1.5 g (3.7 mmol) of 2-{4-[ethyl(2-hydroxyethyl)amino]phenyl}-6-nitro-1H-benzo[de]isoquinolin-1,3(2H)-dione was dissolved in 80 mL of chloroform and heated to a boil. Then, 10.7 mL (11.1 mmol) of phosphorus tribromide was added dropwise within 20 minutes, and the solution was heated at reflux for an additional 2 hours. The mixture was then poured onto ice, and the aqueous phase was extracted with chloroform. The combined organic phases were dried over magnesium sulfate. The purification was performed by column chromatography on silica gel with toluene as the developing solvent. Yield: 0.90 g (52% of the theoretical), dark-red powder. $^1$H-NMR (d$_6$DMSO/300 MHz): δ=1.12 (t, J=8.1 Hz, 3H), 1.86 (q, 2H), 3.58 (t, J=6.9 Hz, 2H), 4.01 (t, J=6.9 Hz, 2H), 6.96 (d, J=4.2 Hz, 2H, phenyl), 7.83 (d, J=7.6 Hz, 1H, naphthalene), 7.95 (d, J=4.4 Hz, 2H, phenyl), 8.33 (d, J=8.1 Hz, 1H, naphthalene), 8.52 (d, J=8.8 Hz, 1H, naphthalene), 8.67 (d, J=8.0 Hz, 1H, naphthalene), 9.13 (d, J=8.6 Hz, 1H, naphthalene).

Step 3: Preparation of 3-{2-[ethyl-4-(6-nitro-1,3-diketo-1H-benzo[de]isoquinolin-2-(3H)-yl)anilino]ethyl}-1-methyl-1H-imidazol-3-ium bromide 0.5 g (1.07 mmol) of 2-{4-[(2-bromoethyl)(ethyl)amino]phenyl}-6-nitro-1H-benzo[de]isoquinolin-1,3-(2H)-dione was dissolved in 40 mL of acetonitrile. After the addition of 0.44 g (5.35 mmol) of N-methylimidazole, the mixture was stirred for 2 hours at reflux. Following removal of the solvent under vacuum, the precipitate was filtered off, washed with ethyl acetate and dried. Yield: 0.32 g (54% of the theoretical), red-brown powder. UV/Vis (DMSO): λ$_{max}$: 409, 520 nm Example 3

Preparation of 2-[(3-methyl-1,3-benzothiazol-2-(3H)-ylidene)amino]-6-nitro-1H-benzo[de]isoquinolin-1,3(2H)-dione The product was obtained as a yellow powder by condensation of 2,3-dihydro-3-methyl-2-benzo-thiazolone hydrazone hydrochloride hydrate with 4-nitronaphthalene-1,8-dicarboxylic anhydride in imidazole (synthesis and work-up as in Example 2, Step 1). The purification was performed by column chromatography on silica gel. UV/Vis (CHCl$_3$): λ$_{max}$: 301, 345 nm Example 4

Preparation of 2-(1,3-benzothiazol-2-yl)-6-nitro-1H-benzo[de]isoquinoline-1,3-(2H)-dione As in Example 3, the product obtained from 2-aminobenzothiazole and 4-nitronaphthalene-1,8-dicarboxylic anhydride in imidazole was isolated as an orange-yellow powder. The purification was performed by column chromatography on silica gel. UV/Vis (CHCl$_3$): λ$_{max}$: 345, 379 nm Example 5

Preparation of 2-{2-[(2-hydroxyethyl)amino]4-methoxyphenyl}-5-nitro-1H-benzo-[de]isoquinolin-1,3(2H)-dione The reaction of N-(2-hydroxyethyl)-5-methoxy-2-aminoaniline with 3-nitronaphthalene-1,8-dicarboxylic anhydride in imidazole (synthesis and work-up as in Example 2, Step 1) afforded the product as a dark-red powder. For purification, the crude product in ethanol/acetone was filtered through a bed of silica gel UV/Vis (CHCl$_3$: λ$_{max}$: 411, 524 nm Example 6

Hair Colorant (Without Oxidant)

| | |
|---|---|
| 2.5 mmol | of dye of general formula (I) |
| 5.0 g | of ethanol |
| 4.0 g | of decylpolyglycose |
| 0.2 g | of disodium ethylenediaminetetraacetate hydrate |
| to 100.0 g | water, demineralized |

The dye solution was adjusted to pH 7 to 10 by addition of ammonia.

The hair was dyed by applying to it a sufficient amount of the colorant, allowing the colorant to act for 30 minutes at 40°

C., rinsing with lukewarm water and drying. The coloring results are summarized in the following Table 1.

Example 7

Hair Colorant (With Oxidant)

| | |
|---|---|
| 0.100 g | of dye of general formula (I) |
| 1.000 g | of potassium persulfate |
| 1.500 g | of ammonium persulfate |
| 1.200 g | of sodium silicate |
| 0.625 g | of magnesium oxide |
| 0.250 g | of hydroxyethylcellulose |
| 0.300 g | of granular soap |
| 0.100 g | of disperse silicic acid |
| 0.025 g | of disodium EDTA |
| 10.000 g | of hydrogen peroxide (12% in water) |

The afore-indicated components were mixed to a uniform composition so that the dye particles could no longer be seen. An amount of the said coloring composition sufficient for hair coloring was then applied to the hair. After an exposure time of 45 minutes at 40° C., the hair was rinsed with lukewarm water, treated with an acidic conditioner, again rinsed and then dried.

The coloring results are summarized in the following Table 1.

TABLE 1

| Example No. | Dye of General Formula (I) | Color |
|---|---|---|
| 6 | 3-{2-[ethyl-4-(6-nitro-1,3-diketo-1H-benzo[de]-Isoquinolin-2(3H)-yl)anilino]ethyl}-1-methyl-1H-imidazol-3-ium bromide | red-orange |
| 7 | 4-{(E)-[(1,3-diketo-2,3-dihydro-1H-benzo[de]-isoquinolin-6-yl)imino]methyl}-1-(2-hydroxy-ethyl)pyridinium bromide | bright-yellow; yellow-green fluorescence under UV excitation |

Example 8

Hair Colorant (with Oxidant and Another Direct Dye)

| | |
|---|---|
| 0.100 g | of 4-{(E)-[(1,3-diketo-2,3-dihydro1H-benzo[de]isoquinolin-6-yl)imino]methyl}-1-(2-hydroxyethyl)pyridinium bromide |
| 0.050 g | of 3',3''',4,5,5',5'',6,7-octabromophenolsulfonphthalein (Tetrabromophenol Blue) |
| 1.000 g | of potassium persulfate |
| 1.500 g | of ammonium persulfate |
| 1.200 g | of sodium silicate |
| 0.625 g | of magnesium oxide |
| 0.250 g | of hydroxyethylcellulose |
| 0.300 g | of granular soap |
| 0.100 g | of disperse silicic acid |
| 0.025 g | of disodium EDTA |
| 10.000 g | of hydrogen peroxide (12% in water) |

The afore-indicated components were mixed to a uniform composition so that the dye particles could no longer be seen. An amount of the foregoing coloring composition sufficient for hair coloring was then applied to the hair. After an exposure time of 45 minutes at 40° C., the hair was rinsed with lukewarm water and then dried. This gave a light-blue coloration.

Example 9

Hair Colorant (with Oxidant and Another Direct Dye)

| | |
|---|---|
| 0.100 g | of 4-{(E)-[(1,3-diketo-2,3-dihydro-1H-benzo[de]isoquinolin-6-yl)imino]-methyl}-1-(2-hydroxyethyl)pyridinium bromide |
| 0.050 g | of 2',4',5'7'-tetrabromo-4,5,6,7-tetrachloro-3',6'-dihydroxyspiro{isobenzofuran-1(3H),9'[9H]xanthen}-3-one disodium salt (Acid Red 92; Cl 45410) |
| 1.000 g | of potassium persulfate |
| 1.500 g | of ammonium persulfate |
| 1.200 g | of sodium silicate |
| 0.625 g | of magnesium oxide |
| 0.250 g | of hydroxyethylcellulose |
| 0.300 g | of granular soap |
| 0.100 g | of disperse silicic acid |
| 0.025 g | of disodium EDTA |
| 10.000 g | of hydrogen peroxide (12% in water) |

The afore-indicated components were mixed to a uniform composition so that the dye particles could no longer be seen. An amount of the said coloring composition sufficient for hair coloring was then applied to the hair. After an exposure time of 45 minutes at 40° C., the hair was rinsed with lukewarm water and then dried. This gave a pink-red coloration.

Unless otherwise indicated, all percentages given in the present patent application are by weight.

The invention claimed is:

1. A naphthalene derivative selected from the group consisting of 3-methyl-2-{5-nitro-2-ketobenzo[cd]indol-1(2H)-yl}-1,3-benzothiazol-3-ium methylsulfate, 2-{5-(dimethylamino)-2-ketobenzo[cd]indol-1(2H)-yl}-3-methyl-1,3-benzothiazol-3-ium methylsulfate, 5-((E)-{1-[4-(dimethylamino)phenyl]-2-keto-1,2-dihydrobenzo-[cd]indol-6-yl}diazenyl)-4-hydroxy-1-(2-hydroxyethyl)-3,6,7-trimethyl-1H-pyrazolo[3,4-b]pyridin-7-ium methylsulfate, 1-{4-[bis(hydroxyethyl)amino]phenyl}-6-nitrobenzo[cd]indol-2(1H)-one, 3-{2-[ethyl-4-(6-nitro-2-ketobenzo[cd]indol-1(2H)-yl)anilino]ethyl}-1-methyl-1H-imidazol-3-ium bromide, 4-{(E)-[(1,3-diketo-2,3-dihydro-1H-benzo[de]isoquinolin-6-yl)imino]-methyl}-1-(2-hydroxyethyl)pyridinium bromide, 2-[4-((E)-{1-[4-(dimethylamino)phenyl]-2-keto-1,2-dihydrobenzo[cd]indol-5-yl}diazenyl) (ethyl) anilino]-N,N,N-trimethylethanaminium bromide, 2-[(3-methyl-1,3-benzothiazol-2(3H)-ylidene)amino]-6-nitro-1H-benzo[de]isoquinolin-1,3(2H)-dione, 2-(1,3-benzothiazol-2-yl)-6-nitro-1H-benzo[de]isoquinolin-1,3(2H)-dione 2-{2-[(2-hydroxyethyl)amino]-4-methoxyphenyl}-5-nitro-1H-benzo[de]isoquinolin-1,3(2H)-dione, and 3-{2-[ethyl-4-(6-nitro-1,3-diketo-1H-benzo-[de]isoquinolin-2(3H)-yl) anilino]ethyl}-1-methyl-1H-imidazol-3-ium bromide.

2. An agent comprising at least one naphthalene derivative as defined in claim 1.

3. An agent as defined in claim 2, and further comprising at least one oxidant.

4. An agent as defined in claim 3, wherein the oxidant is selected from the group consisting of hydrogen peroxide and hydrogen peroxide adducts, persulfates and perborates.

5. An agent as defined in claim 2, wherein the agent contains at least one natural or synthetic polymer or a modified polymer of natural origin commonly used in cosmetic agents.

6. An agent as defined in claim 5, wherein the agent contains the polymer in an amount from 1 to 5 weight percent.

7. An agent as defined in claim 2, wherein the agent contains the naphthalene derivative in an amount from 0.01 to 10 weight percent.

8. An agent as defined in claim 2, wherein the agent is a hair colorant.

* * * * *